(12) United States Patent
Lang

(10) Patent No.: US 6,541,043 B2
(45) Date of Patent: Apr. 1, 2003

(54) METHOD AND SYNERGISTIC COMPOSITION FOR TREATING ATTENTION DEFICIT/HYPERACTIVITY DISORDER

(75) Inventor: Philip C. Lang, Toms River, NJ (US)

(73) Assignee: DexGen Pharmaceuticals, Inc., Manasquan, NJ (US)

( * ) Notice: Subject to any disclaimer, the term of this patent is extended or adjusted under 35 U.S.C. 154(b) by 0 days.

(21) Appl. No.: 09/941,422

(22) Filed: Aug. 28, 2001

(65) Prior Publication Data

US 2003/0044472 A1 Mar. 6, 2003

(51) Int. Cl.[7] ............................ A61K 33/00; A01N 65/00
(52) U.S. Cl. ....................... 424/725; 424/728; 424/730; 424/731
(58) Field of Search ............................. 424/725, 728, 424/730, 731, 1.69, 185.1, 1.73

(56) References Cited

U.S. PATENT DOCUMENTS

| | | | |
|---|---|---|---|
| 3,819,480 A | * 6/1974 | Hochschild | 195/1.8 |
| 5,719,178 A | 2/1998 | Paul et al. | 514/450 |
| 6,056,971 A | * 5/2000 | Goldman | 424/439 |
| 2001/0031757 A1 | * 10/2001 | Shafer et al. | 514/255.05 |

OTHER PUBLICATIONS

JP abstract, JP06311866A, see the entire abstract, Apr. 1993, Derwent–ACC No.: 1995–027241.*

* cited by examiner

*Primary Examiner*—David M. Naff
*Assistant Examiner*—Deborah K. Ware
(74) *Attorney, Agent, or Firm*—DeLio & Peterson, LLC

(57) ABSTRACT

A composition and method for treating Attention Deficit/Hyperactivity Disorder (ADHD) is provided which can be used both with and without ethical drugs now used to treat ADHD. The composition contains dimethylaminoethanol (DMAE), omega 3-fatty acids, betaine, oligomeric proanthocyanidins (OPC), folic acid, vitamins C, E, $B_{12}$, $B_6$, $B_5$ and beta-carotene and minerals (calcium, magnesium, zinc and selenium). Ethical drugs such as amphetamines, methylphenidate HCl and pemoline are known to control ADHD, but each has significant side effects when used in their therapeutic dose. When combining the composition with such ethical drugs, the amount of the ethical drug can be lowered below a level which causes undesirable side effects which is an important feature. Preferred compositions contain one or more of lecithin, choline, 5-hydroxytryptophan, tyrosine, Reishi Extract, Kava Extract, Gingko, Ginseng and St. John's Wort.

20 Claims, No Drawings

US 6,541,043 B2

METHOD AND SYNERGISTIC COMPOSITION FOR TREATING ATTENTION DEFICIT/HYPERACTIVITY DISORDER

BACKGROUND OF THE INVENTION

1. Field of the Invention

The present invention relates to a composition and method for treating Attention Deficit/Hyperactivity Disorder.

2. Description of Related Art

Attention Deficit/Hyperactivity Disorder (ADHD) is the fastest growing childhood disorder in the United States. About four million children and thirteen million adults suffer from attention deficit in the U.S. Diagnostic and Statistical Manual of Mental Disorders (DSM IV) categorization of ADHD includes terms such as "inattention, impulsiveness and hyperactivity". Three subtypes are recognized ADHD: Combined type; ADHD, Predominately Inattentive Type; and ADHD, Predominately Hyperactive/Impulsive Type. The Predominately Inattentive Type makes careless mistakes, cannot keep focused on a task, and loses attention and interest quickly. Often the person appears not to listen as if their mind is "someplace else". The predominately Hyperactive/Impulsive Type is characterized by fidgetiness, excessive unproductive movement, impulsiveness, inappropriate behavior, making noise, impatience, touching things or being disruptive.

Depending on age and development stage, ADHD sufferers may exhibit low frustration tolerance, temper outbursts, stubbornness, making demands, mood lability, rejection by peers and poor self-esteem.

There are no established diagnostic laboratory tests in the clinical assessment of ADHD and it is still not clear what fundamental cognitive deficit is responsible for this disorder.

The current treatment for ADHD is with central nervous stimulants (CNS) stimulants such as methylphenidate hydrochloride (Ritalin), amphetamines (Adderall) or pemoline (Cylert). Regrettably, each of these drugs has frequent and undesirable side effects. Methylphenidate HCl is associated with the following side effects: nervousness, insomnia, hypersensitivity, urticara, fever, arthralgia, anorexia, nausea, dizziness, tachycardia, angina, cardiac arrhythmia, and retarded growth and weight loss during prolonged therapy. Pemoline has been associated with life threatening hepatic failure, convulsive seizures, Gilles de la Tourette syndrome, hallucinations, dyskinetic movements, mild depression, dizziness, and insomnia. Amphetamines are associated with the following side effects: palpitations, tachycardia, elevated blood pressure, pyscotic episodes, over stimulation, restlessness, dizziness, euphoria, dyskinesia, dysphoria, tremors, exacerbation of motor tics and Tourette's syndrome. There is also potential for drug abuse and dependence with these drugs.

Bearing in mind the problems and deficiencies of the prior art, it is therefore an object of the present invention to provide a composition for treating Attention Deficit/Hyperactive Disorder.

A further object of the present invention is to provide a composition which can be used with existing compositions for treating Attention Deficit/Hyperactive Disorder, and preferably with a lower dosage of the existing composition.

It is another object of the present invention to provide a method for treating Attention Deficit/Hyperactive Disorder in a person by administering to the person a composition of the invention.

Still other objects and advantages of the invention will in part be obvious and will in part be apparent from the specification.

SUMMARY OF THE INVENTION

The above and other objects, which will be apparent to those skilled in art, are achieved in the present invention which is directed to a composition comprising a mixture of ingredients and a method for using the composition to treat Attention Deficit/Hyperactivity Disorder. The composition comprises a mixture of ingredients which act synergistically to provide the desired therapeutic effect.

In one aspect, a composition is provided for treating Attention Deficit/Hyperactivity Disorder comprising:

dimethylaminoethanol;

omega-3 fatty acid;

betaine;

Vitamins A, $B_5$, $B_6$, $B_{12}$, C and E;

folic acid;

minerals including calcium, magnesium, zinc and selenium; and oligomeric proanthocyanidins.

In another aspect of the invention the composition further contains lecithin, choline, 5-hydroxytryptophan (5HT) and/or tyrosine.

In a further aspect of the invention the composition further contains Reishi extract.

In another aspect of the invention the composition further contains Kava extract (kavalactone).

In still a further aspect of the invention the composition further contains gingko and/or ginseng.

In another aspect of the invention the composition further contains St. John's Wort.

In a further aspect of the invention the composition contains one or more of the above components, preferably all the above components.

The above compositions may also be used in combination with other known compositions used for treating ADHD including amphetamines, methylphenidate HCl, fluoxatine, sertraline, paroxetine, fluoroxamine, citralopram, venlafaxine, bupropion, nefazodone and mirtazapine. In an important feature of the invention, the known compositions will be used in an amount up to 50% of its normal dose in combination with the composition of the invention thus minimizing side effects of the known composition.

In another aspect of the invention a method is provided for treating Attention Deficit/Hyperactivity Disorder wherein the composition of the invention is administered by oral, sublingual, rapid dissolution tablets, buccal, transdermal, intramuscular and intravenous means. Oral compositions may be formed into a soft-gel article, capsule, tablets, tablets with a coating, sustained release or granular product.

DESCRIPTION OF THE PREFERRED EMBODIMENT(S)

It is apparent that there is a need for the treatment of ADHD without the serious side effects of the aforementioned known drugs now used for treating ADHD. This invention provides a safe and efficacious combination of natural products which can be used with or without a reduced dosage of known ethical drugs used for ADHD.

Dimethylaminoethanol (DMAE) is a natural chemical (found in fish) and has a p-acetamidobenzoate salt formerly prescribed for short attention span and hyperactivity. This drug is now available as an over-the-counter (OTC) nutrient supplement. Unlike most stimulant drugs, which tend to produce a short "up" cycle followed by a quick "come down", DMAE's effects are long lasting and more subtle. People who take DMAE report that after three or four weeks, they feel a mild stimulation continually, without side effects. The quintessential "nootropic" DMAE focuses on specific cortical brain functions associated with the direct intensification of consciousness. Side effects are very rare— high doses may result in insomnia, headache or tense muscles, which disappear if the dose is lowered. No serious adverse effects have been reported with DMAE.

DMAE it is hypothesized accelerates the brain's synthesis and turnover of the neurotransmitter, acetylcholine, by redirecting choline synthesis to the cortex. Acetylcholine is the neurotransmitter that the brain uses for short term and long term memory and also helps in concentrating and focusing. Clinical studies including a double blind clinical study comparing DMAE and Ritalin, demonstrated significant test score improvements for both DMAE and Ritalin vs. placebo in ADHD children. DMAE has been shown to increase levels of choline in the brain due to DMAE's superior ability to cross the Blood-Brain Barrier. DMAE has been shown to elevate mood and allow a sounder sleep. DMAE has also been shown to decrease the accumulation of lipofuscin in the brain and to increase attention span and improved concentration. DMAE and derivatives thereof such as its p-acetamido benzoate salt and its bitartrate salt is an important component in the composition of this invention for treating Attention Deficit/Hyperactivity Disorder. Amounts of DMAE of up to 1000 mg, or more, preferably 200–800 mg are used.

The brain consists of about 60% fat (lipids). In clinical studies with children with Attention Deficit/Hyperactivity Disorder, supplements of omega-3 fatty acids [eicosapentaenoic acid (EPA), and docosahexanoic acid (DHA)] vs. placebo, have demonstrated improved mood, enhanced clarity of thinking, more serenity and mental clarity of thinking, better concentration and better vision for those taking omega-3 fatty acids. Omega-3 fatty acids (e.g., EPA and DHA; fish oil) are an important component of the composition of the invention and are used in an amount of up to about 1200 mg or more, preferably 200–800 mg.

Since the brain contains so much fat (lipids), it is hypothesized the brain has to be protected from free radicals forming "lipid peroxidation" which can cause brain disorders. Antioxidants such as vitamin C, E and A, preferably beta-carotene, improve memory performance and are included in the composition of the invention for this purpose. Vitamin C is used in an amount up to about 1500 mg or more, preferably 200–1000 mg; vitamin E up to about 800 IU or more, preferably 400 IU; and Vitamin A up to about 25,000 IU or more, preferably 10,000–25,000 IU.

Recently, U.S. Pat. No. 5,719,178 claimed the use of proanthocyanidins (derived from the conifer bark), an antioxidant, in the treatment of APHD. The general class of oligomeric proanthocyanidins (OPC), which include conifer bark extract, grape seed extract, pine bark extract and the protective phenolic compounds from natural sources including bioflavonoids it is hypothesized can reduce free radical damage causing APHD and are included in the composition of the invention. These "free radical inhibitors" can pass through the Blood-Brain Barrier to protect the brain. OPCs have been shown to possess antihistamine, anti-inflammatory and immune-boosting effects as well as inhibiting the breakdown of the catecholamine neurotransmitters. OPCs increase attention span, increase focus and decrease emotional activity in ADHD persons and are used in the composition of the invention in an amount of about 200 mg or more, preferably 50–150 mg.

Faulty neurotransmission is considered the main reason for ADHD. Acetylcholine is involved with learning and memory. Serotonin is involved with mood, emotional balance and impulse control. Catecholamines speed up the rate at which one neuron signals another. It is an important feature of this invention that there be a proper balance between the neurotransmitters for "normal" mental and emotional function. ADHD is a complex disorder involving an unbalance in several neurotransmitters. This invention uses a multi-step approach to fully treat ADHD disorder and the body according to this invention must have "methyl donors" to synthesize the brain chemicals, which accounts for their mood elevating and cognitive effects. Betaine or trimethylglycine, folic acid and vitamin $B_{12}$ are methyl donors, which are included in the composition of the invention. Betaine is used in an amount up to about 750 mg or more, preferably 100–500 mg. Folic acid is used in an amount up to 1.2 mg or more, preferably 0.4–1 mg and Vitamin $B_{12}$ up to about 40 mcg or more, preferably 3–30 mcg.

In addition to the vitamins mentioned, the body uses vitamin $B_5$ to form acetylcholine and vitamin $B_6$ to form serotonin and L-Dopa into Dopamine, which accounts for their effect of increased alertness and mood. These vitamins are included in the composition of the invention. Vitamin $B_5$ is used up to about 250 mg or more, preferably 50–250 mg and Vitamin $B_6$ up to about 25 mg or more, preferably 5–25 mg.

There are some vital minerals that affect the functioning of the brain. Calcium is a second messenger in neuronal membranes and it acts like a traffic signal for uptake and release of neurotransmitters. A "green light" from calcium permits release of a neurotransmitter into the synaptic intersection and a "red light" halts its passage into the receiving neuron. Calcium regulates the speed, intensity and clarity of every message that passes between brain cells. Magnesium is the second most important mineral in the brain. A study found low magnesium levels in 95% of ADHD children. Supplements of magnesium at a level of 6 mg/lb. of the child showed a decrease in hyperactivity. Zinc is the third most important mineral in the brain, where it acts like an antioxidant and also acts on the surface of the neurons as an electrical "contact" for neurotransmission. Selenium has been shown to protect the integrity of message sending between neurons by preventing free-radical attacks. One or more of these minerals, preferably all, are included in the composition of the invention in amounts up to about 150% of their RDA or more, preferably 100%. Calcium is preferably used at a level of 200 to 1200 mg, magnesium 100 to 500 mg, zinc 5 to 50 mg and selenium 40 to 120 mcg.

5-Hydroxytryptophan (5-HT), the precursor of serotonin, is also included in a preferred composition of the invention in an amount up to 75 mg or more, preferably 25–50 mg. Tyrosine, an amino acid, is a precursor of the catecholamines and used as a food supplement and improves alertness and elevated mood. Tyrosine is included in the composition of the invention in an amount up to 300 mg or more, preferably 50–250 mg.

Like omega-3 fatty acids, phospholipids are important for optimal brain health, and are found in high concentrations in the brain. They help the brain cells communicate and influence how well the receptors function. Lecithin is a phospholipid found in certain foods and available as a food implement. Lecithin provides a very available source of choline required for acetylcholine. Lecithin and cytidine 5-diphosocholine (CDP) supplements increase alertness and motivation. Lecithin is used in an amount up to 2000 mg or more, preferably 600–1800 mg. Choline is also included in a preferred composition of the invention in an amount up to 800 mg or more, preferably 100–500 mg.

Another important component of a preferred composition of the invention is Reishi extract derived from mushrooms. Reishi extract calms the mind, eases tension, improves memory and sharpens concentration and focus which are all important effects for treating Attention Deficit/Hyperactivity Disorder according to this invention. Reishi extract is used in an amount up to 2000 mg or more, preferably 500–1500 mg.

Kava (*Piper Methysticum*) is a plant grown in the South Pacific and contains kavalactones, which influence a number of brain receptors involved with relaxation and mental clarity. In a study the results showed kava superior to placebo, with improvements in anxiety, mood, tension and fears with increased alertness. With the anxiety that is part of ADHD, kava extract is included in the composition to provide a calming effect and increase concentration. Kava is used in an amount up to 200 mg or more, preferably 50–150 mg.

Gingko Biloba extract contains flavonoids and terpene lactones. Gingko improves communication between nerve cells and enhances blood flow to the brain. It also acts as a powerful antioxidant. Ginseng extract has been found to improve blood circulation and provide mental clarity. Researchers have evaluated the cognitive effects of gingko/ginseng. A double blind, placebo controlled study showed improvements in memory and overall cognitive function for those taking both gingko and ginseng and both are in preferred embodiments of the invention. Gingko is used in an amount up to 200 mg or more, preferably 30–120 mg and Ginseng up to about 200 mg or more, preferably 50–150 mg.

The herb, St. John's Wort, affects five neurotransmitters in the brain: serotonin, noradrenaline, dopamine, gamma-aminobutyric acid (GABA) and interleukin-6. Because St. John's Wort affects these neurotransmitters, it helps balance them to provide "normality" and is a preferred component in the composition of the invention for treating ADHD in an amount up to about 800 mg or more, preferably 100–600 mg.

In the combination of the aforementioned "natural" therapy, with ethical drugs, in addition to amphetamines, methylphenidate HCl, and pemoline, the composition of the invention can be used also with fluoxetine, sertraline, paroxetine, fluoxamine, citalopram, venlafaxine, bupropion, nefazodone and mirtazapien, among others.

While the above components as described are the preferred components to be used in the composition of the invention it will be appreciated to those skilled in the art that known derivatives, e.g., salts, may be employed.

As set forth hereinabove, it is an important feature of the invention that the components act together to provide a synergistic effect by effecting different pathways of action, i.e., by normalizing the several neurotransmitters and receptor sites responsible for ADHD.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A composition for treating Attention Deficit/Hyperactivity Disorder consisting essentially of:
    dimethylaminoethanol;
    omega-3 fatty acid;
    betaine;
    Vitamins A, $B_5$, $B_6$, $B_{12}$, C and E;
    folic acid;
    minerals including calcium, magnesium, zinc and selenium; and
    oligomeric proanthocyanidins.
2. The composition of claim 1 further containing lecithin, choline, 5-hydroxytryptophan and/or tyrosine.
3. The composition of claim 2 further containing Reishi extract.
4. The composition of claim 3 further containing Kava extract.
5. The composition of claim 4 further containing gingko and/or ginseng.
6. The composition of claim 5 further containing St. John's Wort.
7. The composition of claim 1 further containing Reishi extract.
8. The composition of claim 7 further containing Kava extract.
9. The composition of claim 8 further containing gingko and/or ginseng.
10. The composition of claim 9 further containing St. John's Wort.
11. The composition of claim 1 further containing Kava extract.
12. The composition of claim 11 further containing gingko and/or ginseng.
13. The composition of claim 12 further containing St. John's Wort.
14. The composition of claim 1 further containing gingko and/or ginseng.
15. The composition of claim 14 further containing St. John's Wort.
16. The composition of claim 1 further containing St. John's Wort.
17. A method for treating Attention Deficit/Hyperactivity Disorder comprising administering to a person having said disorder the composition of claim 1.
18. The composition of claim 1 further containing for Attention Deficit/Hyperactivity Disorder selected from the group consisting of amphetamines, methylphenidate HCl, fluoxatine, sertraline, paroxetine, fluoroxamine, citalopram, venlafaxine, bupropion, nefazodone, mirtazapine and mixtures thereof.
19. The composition of claim 18 wherein the drug is in an amount of up to 50% of its normal dose.
20. A method for treating Attention Deficit/Hyperactivity Disorder comprising administering to a person having said disorder the composition of claim 18.

* * * * *